(12) United States Patent
Mohr et al.

(10) Patent No.: US 9,328,049 B2
(45) Date of Patent: May 3, 2016

(54) HYDROCARBON CONVERSION PROCESS

(71) Applicant: ExxonMobil Chemical Patents Inc., Baytown, TX (US)

(72) Inventors: Gary D. Mohr, Houston, TX (US); Paul F. Keusenkothen, Houston, TX (US); Frank Hershkowitz, Basking Ridge, NJ (US); Jonathan M. McConnachie, Annandale, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 86 days.

(21) Appl. No.: 13/865,247

(22) Filed: Apr. 18, 2013

(65) Prior Publication Data

US 2013/0310601 A1 Nov. 21, 2013

Related U.S. Application Data

(60) Provisional application No. 61/648,987, filed on May 18, 2012.

(30) Foreign Application Priority Data

Jun. 29, 2012 (EP) ..................... 12174340

(51) Int. Cl.
| | | |
|---|---|---|
| *C07C 51/16* | (2006.01) | |
| *C07C 2/48* | (2006.01) | |
| *C07C 51/285* | (2006.01) | |
| *C10G 45/68* | (2006.01) | |
| *C10G 50/00* | (2006.01) | |
| *C10G 57/02* | (2006.01) | |
| *C10G 9/00* | (2006.01) | |
| *C07C 2/82* | (2006.01) | |
| *B01J 8/04* | (2006.01) | |
| *B01J 19/24* | (2006.01) | |
| *B01J 8/02* | (2006.01) | |
| *C07C 11/24* | (2006.01) | |
| *C07C 13/267* | (2006.01) | |

(Continued)

(52) U.S. Cl.
CPC ............... *C07C 51/16* (2013.01); *B01J 8/0278* (2013.01); *B01J 8/0438* (2013.01); *B01J 8/0442* (2013.01); *B01J 8/0492* (2013.01); *B01J 8/0496* (2013.01); *B01J 19/2485* (2013.01); *C07C 2/48* (2013.01); *C07C 2/82* (2013.01); *C07C 11/24* (2013.01); *C07C 13/267* (2013.01); *C07C 51/285* (2013.01); *C10B 55/00* (2013.01); *C10G 9/00* (2013.01); *C10G 45/68* (2013.01); *C10G 50/00* (2013.01); *C10G 57/02* (2013.01); *B01J 23/26* (2013.01); *C07C 2101/18* (2013.01)

(58) Field of Classification Search
None
See application file for complete search history.

(56) References Cited

U.S. PATENT DOCUMENTS 2,903,491 A 9/1959 Reppe et al.
2,951,881 A 9/1960 Reppe et al.
(Continued)

OTHER PUBLICATIONS

Fray et al., "The Chemistry of Cyclo-octatetraene and its Derivatives", 1978, pp. 19-20, Cambridge University Press, XP002684066.
(Continued)

*Primary Examiner* — Clinton Brooks
*Assistant Examiner* — Jennifer C Sawyer

(57) ABSTRACT

The invention relates to processes for converting hydrocarbons to phthalic acids such as terephthalic acid. The invention also relates to polymerizing phthalic acid derivatives to produce, e.g., synthetic fibers.

21 Claims, 4 Drawing Sheets

(51) Int. Cl.
*C10B 55/00* (2006.01)
*B01J 23/26* (2006.01)

(56) References Cited

U.S. PATENT DOCUMENTS 4,724,272 A * 2/1988 Raniere .................... C10G 9/38
  208/129
2007/0144940 A1  6/2007 Hershkowitz 2007/0191664 A1 * 8/2007 Hershkowitz et al. ........ 585/539
2008/0142409 A1  6/2008 Sankaranarayanan et al.
2010/0234637 A1 * 9/2010 Fong et al. .................... 562/412
2013/0296620 A1  11/2013 Mohr et al.

OTHER PUBLICATIONS

Ganellin, C.R. et al, Journal of the American Chemical Society, vol. 79, No. 7, Apr. 5, 1957, pp. 1767-1768.

* cited by examiner

HYDROCARBON CONVERSION PROCESS

PRIORITY CLAIM

The present application claims priority to and the benefit of U.S. Ser. No. 61/648,987 filed on May 18, 2012 and EP Application No. 12174340.5 filed Jun. 29, 2012 and entitled, "Hydrocarbon Conversion Process," the disclosure of which is hereby incorporated by reference herein in its entirety.

FIELD OF THE INVENTION

The invention relates to processes for converting hydrocarbons to phthalic acids, such as terephthalic acid. The invention also relates to polymerizing phthalic acid derivatives to produce, e.g., synthetic fibers.

BACKGROUND OF THE INVENTION

Aromatic hydrocarbons, such as benzene, toluene, xylene, etc., are useful as fuels, solvents, and as feeds for various chemical processes. Of the xylenes, para-xylene ("p-xylene") is particularly useful for manufacturing phthalic acids such as terephthalic acid, which is an intermediate in the manufacture of synthetic fibers, such as polyester fibers.

Xylenes can be produced from naphtha by processes such as steam cracking. Besides p-xylene, the $C_8$ aromatic portion of a steam cracker effluent generally contains significant amounts of orthoxylene, metaxylene, and ethylbenzene. These molecules all have similar boiling points, which lead to difficulties in separating the p-xylene for conversion to terephthalic acid. Conventional methods for separating $C_8$ aromatics generally utilize complex, high-cost, energy-intensive separations process, e.g., those utilizing superfractionation and/or multistage refrigeration steps.

It is desirable to produce terephthalic acid from hydrocarbon with fewer/less stringent separations.

SUMMARY OF THE INVENTION

In an embodiment, the invention relates to a hydrocarbon conversion process, comprising:
(a) providing a first mixture comprising ≥1.0 wt. % hydrocarbon based on the weight of the first mixture;
(b) exposing the first mixture to a temperature≥700° C. under pyrolysis conditions to produce a second mixture, wherein (i) the second mixture comprises ≥1.0 wt. % acetylene based on the weight of the second mixture and (ii) ≥95.0 wt. % of the second mixture's acetylene, based on the weight of the second mixture's acetylene, is produced by conversion of at least a portion of the first mixture's hydrocarbon;
(c) converting ≥10.0 wt. % of the second mixture's acetylene to cyclooctatetraene, based on the weight of the second mixture's acetylene, in order to produce a third mixture, the third mixture comprising at least a portion of the cyclooctatetraene produced by the acetylene conversion; and
(d) converting ≥5.0 wt. % of the third mixture's cyclooctatetraene to water and phthalic acids, based on the weight of the third mixture's cyclooctatetraene.

DETAILED DESCRIPTION

Figure 1:
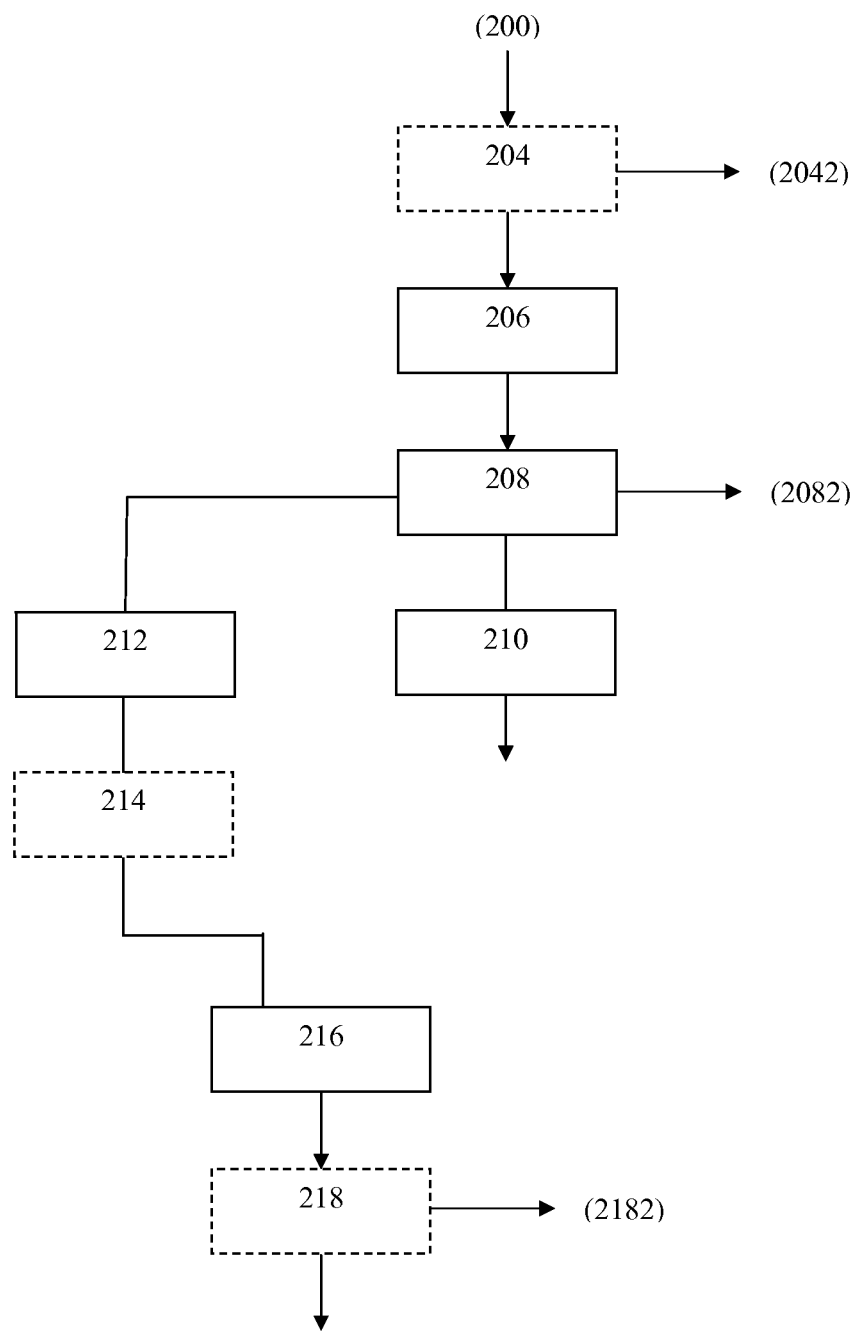
FIG. 1 schematically illustrates one embodiment of the invention including optional stages (enclosed by dashed lines) for separating cyclooctatetraene and for separating phthalic acid.

The invention relates to a process for producing phthalic acids, such as terephthalic acid, from hydrocarbon, such as methane and/or heavy oil. Pyrolysis can be utilized for converting at least a portion of a first mixture comprising hydrocarbon to a second mixture, the second mixture comprising ≥1.0 wt. % acetylene based on the weight of the second mixture. At least a portion of the second mixture's acetylene can then be converted to cyclooctatetraene, to produce a third mixture, the third mixture comprising at least a portion of the cyclooctatetraene that is produced by the converting of the acetylene. For example, the third mixture can comprise ≥10.0 wt. %, e.g., ≥50.0 wt. %, such as ≥90.0 wt. % of the cyclooctatetraene that is produced by the converting of the acetylene. At least a portion of the third mixture's cyclooctatetraene, e.g., ≥5.0 wt. % based on the weight of the third mixture's cyclooctatetraene, can be converted to a product comprising water and phthalic acid, such as terephthalic acid.

The pyrolysis is generally conducted under thermal pyrolysis conditions. Conventional methods can be utilized for separating acetylene from the second mixture, e.g., by contacting the second mixture with an extraction diluent having an affinity for acetylene, such as a polar solvent, such as n-methylformamide. Acetylene recovered from the extract can be exposed to a catalyst comprising nickel to produce a third mixture comprising cyclooctatetraene. The process conditions can be, e.g., the same as those disclosed in U.S. Pat. Nos. 2,903,491 and 2,951,881, which are incorporated by reference herein in its entirety.

Conventional processes can be utilized for producing the phthalic acid, e.g., by exposing at least a portion of the third mixture's cyclooctatetraene to oxidant and at least one catalyst comprising chromic acid to produce $C_8O_4H_{10}$ (4,5-dihydroxycyclohepta-2,6-dienecarboxylic acid). Suitable methods for converting at least a portion of the cyclooctatetraene to phthalic acid are described in The Chemistry of Cyclo-octatetraene and its Derivatives; G. L. Fray and R. G. Saxton, Cambridge University Press 1978; pp. 19-21; e.g., by subjecting the $C_8O_4H_{10}$ to a pinacol-pinacolone rearrangement utilizing an acid, such as chromic acid to produce $C_8O_3H_8$, with at least a portion of the $C_8O_3H_8$ being oxidized to produce a product comprising water and phthalic acids, e.g., terephthalic acid.

It has been observed that pyrolysing a first mixture comprising ≥1.0 wt. % oxygenate based on the weight of the first mixture, leads to an increase in the second mixture's acetylene:ethylene molar ratio, resulting in (i) an increased cyclooctatetraene yield and (ii) a less than expected increase in the second mixture's $CO_2$ content. Relatively high acetylene:ethylene molar ratios can be achieved, e.g., by exposing the first mixture to a maximum temperature≤1400° C. during the pyrolysis, wherein (i) the first mixture's hydrocarbon comprises ≥10.0 wt. % alkane (including isoalkane) having from 1 to 10 carbon atoms (e.g., 2 to 10), the weight percent being based on the weight of the first mixture's hydrocarbon, and (ii) the first mixture further comprises ≥1.0 wt. % oxygenate, based on the weight of the first mixture. Optionally, the oxygenate comprises ≥90.0 wt. % water, at least a portion of the water being obtained from the product.

Since the process does not require separating $C_8$ aromatics, phthalic acid can be produced at a greater yield and with reduced complexity over the prior art processes, such as steam cracking. And since the pyrolysis can be operated efficiently at a high temperature, e.g., ≥1200° C., the process can produce phthalic acid from a wider range of hydrocarbon feeds, including methane and/or heavy oil, than can the prior art steam cracking processes.

For the purpose of this description and appended claims, the following terms are defined. The term "hydrocarbon" means molecules (and mixtures thereof) including both carbon atoms and hydrogen atoms, and optionally including other atoms (heteroatoms) such as oxygen, sulfur, and nitrogen, wherein the carbon atoms and hydrogen atoms together comprise ≥75.0% of the atoms present in the molecule or mixture of molecules, but excluding molecules comprising ≥10.0 atom % of oxygen atoms. The term "oxygenate" means (i) oxygen atoms and (ii) molecules (and mixtures thereof) which include at least one oxygen atom wherein the oxygen atoms comprise ≥10.0 atom % based on the number of atoms present in the molecule or mixture of molecules, including those molecules which further comprise hydrogen, carbon, sulfur, and nitrogen. The term "molecular hydrogen" means $H_2$. The term molecular oxygen means $O_2$.

The "Periodic Table of the Elements" means the Periodic Chart of the Elements as tabulated on the inside cover of The Merck Index, 12th Edition, Merck & Co., Inc., 1996.

The term "pyrolysis" means an endothermic reaction conducted at a temperature sufficient for thermally breaking C—C or C—H bonds, optionally aided by a catalyst, e.g., the conversion of hydrocarbons to unsaturates, such as ethylene and acetylene. The terms "reactor", "reactor system", "regenerator", "recuperator", "regenerative bed", "monolith", "honeycomb", "reactant", "fuel", and "oxidant" have the meanings disclosed in U.S. Pat. No. 7,943,808, which is incorporated by reference herein in its entirety. The term "pyrolysis reactor", as used herein, refers to a reactor, or combination or system thereof for converting hydrocarbons by at least pyrolysis. The term pyrolysis reactor encompasses, e.g., the combination and system of first and second pyrolysis reactors described in U.S. Pat. No. 7,943,808. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor. The pyrolysis region can include, e.g., one or more conduits, channels, or passages. The term "conduit" refers to means for conducting a composition from one location to another. The term encompasses (i) elementary conducting means, such as a pipe or tube, and (ii) complex means, such as tortuous pathways through conducting means, e.g., pipes, tubes, valves, and reactors, that are filled with random packing. The term "passage" means a geometrically contiguous volume element that can be utilized for conveying a fluid within a reactor, regenerator, recuperator, regenerative bed, monolith, honeycomb, etc. The term "channel" means a plurality of passages that can be utilized together for conveying a fluid within the reactor, regenerator, recuperator, regenerative bed, monolith, honeycomb, etc. For example, a honeycomb monolith can comprise a single channel, the channel having a plurality of passages or sets of passages, e.g., hundreds of thousands of passages per square meter of the honeycomb's cross-section.

The term "pyrolysis stage" means at least one pyrolysis reactor, and optionally means for conducting one or more feeds thereto and/or one or more products away therefrom. The term "thermal pyrolysis" means <50.0% of the heat utilized by the pyrolysis is provided by (a) exothermically reacting the pyrolysis feed, e.g., by exothermically reacting an oxidant with hydrocarbon and/or hydrogen in the pyrolysis feed and/or (b) contacting the pyrolysis feed with the gaseous and/or liquid products of combustion to heat the pyrolysis feed. For example, in thermal pyrolysis≥50.0% of the heat utilized by the pyrolysis is provided by heat transfer from reactor components, e.g., solid surfaces associated with a pyrolysis reactor; optionally ≥80.0% or ≥90.0% of the heat utilized by the pyrolysis is provided by such heat transfer. Optionally, exothermic oxidation, e.g., combustion, occurs within the thermal pyrolysis reactor.

The term "high-severity" with respect to pyrolysing a pyrolysis feed, such as the first mixture, means pyrolysis conditions resulting in the conversion of the mixture to make a product having an acetylene content≥10.0 wt. % based on the weight of the hydrocarbons in the pyrolysis feed. The term "peak pyrolysis gas temperature" means the maximum temperature achieved by the bulk pyrolysis stream gases as they travel through the pyrolysis reactor (e.g., a cracking region or radiant region). One skilled in the art will appreciate that temperatures immediately proximate to a partition may be higher, and may, in some infinitesimal layer, actually approach the partition's temperature. However, the pyrolysis temperature referred to herein should be considered a bulk gas temperature, which is a temperature that could be measured by a device (such as a thermocouple) that is not in contact with the partition. For example, if the gas is traveling through tubulars in a thermal pyrolysis reactor, the bulk gas temperature may be taken as the average temperature over any tubular cross-section, and the peak pyrolysis gas temperature as the highest cross-sectional average temperature of the pyrolysis stream.

In an embodiment, a second mixture is derived by thermal pyrolysis of a first mixture, the first mixture being derived from one or more source materials. The term "source materials" means one or more sources comprising hydrocarbon, including, e.g., one or more of petroleum-derived streams; syngas (a mixture comprising carbon monoxide and hydrogen); methane; methane-containing streams, such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety.

Optionally, one or more mixtures and/or source materials comprises hydrogen atoms. The term "hydrogen content" of a mixture or source material means atomic hydrogen bound to carbon and/or heteroatoms covalently bound thereto and which excludes molecular hydrogen ($H_2$) in the mixture (or source material) expressed as a weight percent based on the weight of the hydrocarbons in the mixture (or source material). Optionally, one or more mixtures and/or source materials comprises non-volatiles. The term "non-volatiles" means molecules and mixtures thereof having a nominal atmospheric boiling point≥570.0° C., e.g., refractory oxygenates, refractory hydrocarbon, metals, minerals, etc. American Society of Testing and Materials ("ASTM") methods can be used to determine the nominal atmospheric boiling point (ASTM method 1078) and the amount and properties of such non-volatiles, such as ASTM methods D-6560, D-7061, D-189, D-482, D-524, and D-2415. Non-volatiles that are capable of being combusted are called "combustible non-volatiles". The term non-volatiles encompasses e.g., coke, ash, soot, resid, metal, mineral, ash-forming asphaltenic, tar, etc., including those formed, e.g., during or after oxidation (e.g., combustion or partial oxidation) and/or pyrolysis, including those which may remain as a residue or deposit in the reaction region. The term "$C_2$ unsaturates" means hydrocarbon having two carbon atoms and two or four hydrogen atoms.

In certain embodiments, the invention relates to a process for converting a first mixture comprising hydrocarbon by exposing the first mixture a temperature≥$1.20 \times 10^{3\circ}$ C. under pyrolysis conditions to produce a second mixture, wherein the second mixture comprises ≥1.0 wt. % acetylene, based on the weight of the second mixture (the pyrolysis step). The process further comprises producing a third mixture by converting at least a portion (e.g., ≥10.0 wt. %) of the second mixture's acetylene to cyclooctatetraene, the third mixture comprising at least a portion of the cyclooctatetraene produced by the acetylene conversion. At least a portion of the third mixture's cyclooctatetraene is then converted to a product comprising water and phthalic acid, such as terephthalic acid. A pyrolysis process useful for producing a second mixture will now be described in more detail. The invention is not limited to this type of pyrolysis, and this description is not meant to foreclose the use of other types of pyrolysis processes within the broader scope of the invention.

Representative Embodiments

One embodiment is illustrated schematically in FIG. 1. A source material 200 is conducted to stage 204, the source material comprising hydrocarbon and optionally oxygenate. For example, the source material can comprise ≥10.0 wt. % of methane, e.g., ≥25.0 wt. % methane, such as ≥50.0 wt. % methane based on the weight of the source material. Optionally, the source material further comprises at least one oxygenate that is useful for producing the first mixture, such as water and/or carbon dioxide. For example, the source material can further comprise ≥1.0 wt. % of at least one oxygenate, e.g., ≥10.0 wt. %, such as ≥25.0 wt. %, based on the weight of the first source material. Examples of representative source materials include one or more of hydrocarbon derived from petroleum; syngas (a mixture comprising carbon monoxide and hydrogen); methane; methane-containing streams, such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety.

The source material can be upgraded in stage 204 to produce the first mixture, e.g., by removing at least a portion of any undesired heteroatom-containing molecules contained in the source material. Such undesired species can be conducted away from stage 204 by conduit 2042. When optional stage 204 is not used, the first mixture can be conducted directly to stage 206, where the first mixture is exposed to a temperature≥700° C. under pyrolysis conditions to produce a second mixture. The second mixture generally comprises ethylene, molecular hydrogen, and ≥1.0 wt. % acetylene based on the weight of the second mixture; the second mixture's acetylene being derived from the first mixture's hydrocarbon by the pyrolysis. Heat for the pyrolysis can be obtained from the exothermic reaction of fuel and oxidant components of a fourth mixture, with a fifth mixture comprising products of the endothermic reaction being conducted away.

Although the embodiment of FIG. 1 shows the first mixture being derived from one source material 200, this is not required, and in other embodiments, the first mixture is derived from a plurality of source materials, e.g., at least one hydrocarbon source material and optionally at least one oxygenate source material. Optionally, one or more of these source materials is upgraded, e.g., in optional upgrading stages 204a, 204b, etc. (not shown), and with the upgraded effluents being utilized for producing the first mixture.

Figure 2:
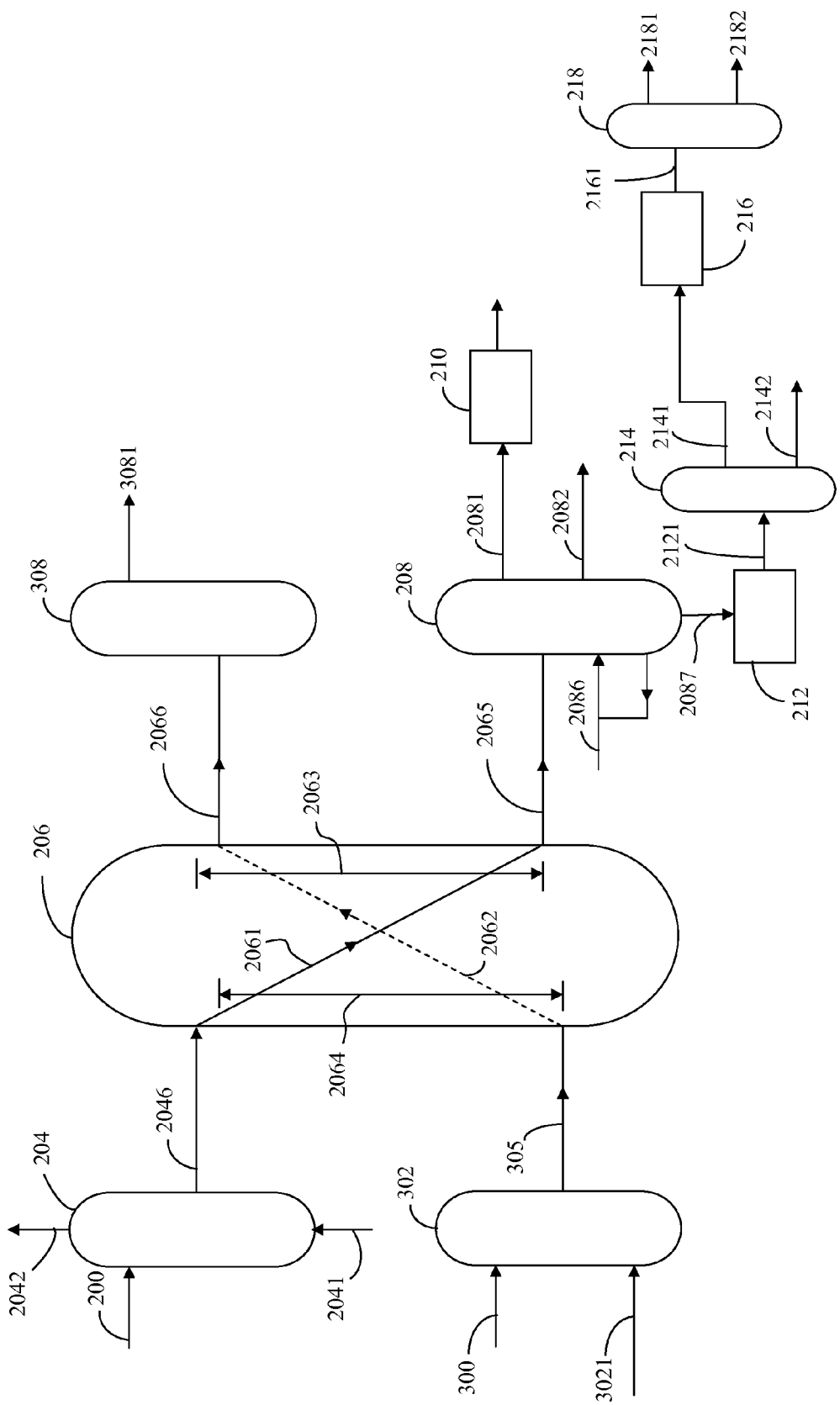
FIG. 2 schematically illustrates an embodiment of the invention utilizing a reverse-flow pyrolysis reactor.

At least a portion of the second mixture, e.g., at least a portion of the second mixture's volatile components, is conducted from stage 206 to stage 208, as shown in FIG. 1. Stage 208 is utilized for separating from the second mixture at least a portion of the second mixture's acetylene, this being conducted away via one or more conduits 2087 (e.g., as shown in FIG. 2). The remainder of the second mixture (following acetylene separation) generally comprises (i) at least a portion of the second mixture's ethylene and (ii) at least a portion of the second mixture's molecular hydrogen. The remainder can be conducted away from stage 208 via one or more conduits 2081. When the first mixture comprises oxygenate, the remainder can further comprise oxygenates converted in stage 206 and unconverted oxygenate. Stage 208 can also be utilized for removing from the second mixture non-volatile components, such as soot and/or heteroatom-containing components, such as hydrogen sulfide, etc., which are not needed in the downstream steps of the process. These components can be removed before and/or after separation of the second mixture's acetylene, and can be conducted away via one or more conduits 2082, as shown.

Solvent extraction can be utilized for removing the second mixture's acetylene. The extract (containing the solvent and acetylene) can be conducted from stage 208 to stage 212, e.g., via one or more conduits 2087. The raffinate, comprising, e.g., the remainder of the second mixture, can be conducted away from stage 208 via one or more conduits 2081.

Optional stage 210 can be utilized for converting at least a portion of the raffinate's ethylene to, e.g., polyethylene, the polyethylene being conducted away from the process via one or more conduits 2120. When the raffinate further compromises molecular hydrogen and carbon monoxide, these can be utilized with at least a portion of the raffinate's ethylene for producing, e.g., ethylene glycol, polyethylene glycol, propylene (by hydroformylating the ethylene with methanol, the methanol being synthesized from the hydrogen and carbon monoxide), polypropylene, etc.

Following recovery of at least a portion of the solvent, e.g., in stage 212, at least a portion of the extract's acetylene is converted to cyclooctatetraene and optionally other aromatics, such as benzene. Optional stage 214 can be utilized for removing at least a portion of the cyclooctatetraene produced during acetylene conversion. Stage 214 can also be utilized for removing, e.g., unreacted acetylene, benzene, saturated molecules, molecular hydrogen, etc., which can be conducted away via one or more conduits 2142. At least a portion of the cyclooctatetraene produced in stage 212 is conducted to stage 214, where at least a portion of the cyclooctatetraene is converted to phthalic acid, such as terephthalic acid, and water.

Optional stage 218 can be utilized for separating at least a portion of the phthalic acid produced in stage 216, the separated phthalic acid being conducted away from the process via one or more conduits 2181, e.g., for conversion to synthetic fiber, such as polyester fibers. Optionally, at least a portion of the water produced in stage 216 is separated in stage 218 and conducted away via one or more conduits 2182. At least a portion of the separated water can be utilized for producing the first mixture, e.g., to increase the second mixture's acetylene:ethylene molar ratio.

In one embodiment, stage 206 comprises at least one regenerative, reverse-flow thermal pyrolysis reactor system. This reactor system; representative first, and fourth mixtures utilized in such a reactor system; representative second, third, and fifth mixtures produced in such a reactor system; and representative downstream process steps that are compatible with these will now be described in more detail. Although the following embodiments are described in terms of a regenerative, reverse-flow pyrolysis reactor system, the invention is not limited thereto, and this description is not meant to foreclose other embodiments within the broader scope of the invention.

Representative Embodiment Utilizing a Regenerative, Reverse-flow Pyrolysis Reactor System An embodiment utilizing a regenerative, reverse-flow thermal pyrolysis reactor system is illustrated schematically in FIG. 2. The first mixture is derived from one or more source materials 200 (e.g., as described above), the source materials optionally being upgraded in optional preparation stage 204. So that the first mixture has the desired composition, preparation stage 204 can be utilized for one or more of (i) separating and conducting away via conduit 2042 one or more of heteroatom-containing molecules, such as hydrogen sulfide, hydrocarbon, non-combustible nonvolatiles, oxygenate, molecular hydrogen, or diluent from the source material, (ii) adding via conduit 2041 one or more of hydrocarbon, oxygenate, molecular hydrogen, or diluent to the source material, (iii) thermally upgrading (e.g., coking or visbreaking) the source material, or (iv) catalytically upgrading (e.g., hydroprocessing, such as hydrotreating) the source material, etc. When utilized in connection with one or more of (ii)-(iv), added hydrocarbon, oxygenate, molecular hydrogen, or diluent can be obtained, e.g., from sources external to the process (such as a syngas generation process) or from sources internal to the process when these species are present in excess of that needed for the downstream steps. For example, light saturated hydrocarbon, such as methane; diluent; excess molecular hydrogen; and/or excess oxygenate (e.g., excess carbon monoxide and/or water) can be obtained from the product of stage 216, the product of stage 210, or from one or more of the second, third, or fifth mixtures.

Preparation stage 204 is optional. In other words, the first mixture can comprise (or consist essentially of, or even consist of) hydrocarbon obtained directly from source material(s) 200, such as natural gas, optionally with no intervening process steps.

The First Mixture

In an embodiment, the first mixture comprises hydrocarbon and optionally further comprises molecular hydrogen, oxygenate, and/or diluent. The first mixture can be derived from the source material(s) located upstream of the pyrolysis, but this is not required. For example, in one embodiment hydrocarbon derived from a first source material and molecular hydrogen derived from a second source material are conducted separately to the pyrolysis reactor, the hydrocarbon and molecular hydrogen being combined to produce the first mixture proximate to (e.g., within) the pyrolysis reactor. The type of hydrocarbon is not critical, e.g., the hydrocarbon can even comprise hydrocarbon non-volatiles, including those that are not in the gas phase at the temperature, pressure, and composition conditions subsisting at the inlet to the pyrolysis reactor. Generally, the hydrocarbon does not contain acetylene, e.g., the first mixture contains ≤0.1 wt. % of acetylene based on the weight of the first mixture. Optionally, the hydrocarbon has (or is derived from one or more source materials having), e.g., a hydrogen content (i) in the range of 6.0 wt. % to 25.0 wt. %, 8.0 wt. % to 20.0 wt. %, or (ii) in the range of 20.0 wt. % to 25.0 wt. %. Hydrogen content is determined in accordance with ASTM D4808-01 (2006). In a particular embodiment, the hydrocarbon of the first mixture is derived from (i) natural gas (e.g., a methane-containing gas of synthetic and/or geological origin) and/or (ii) aromatic gas oil ("AGO", wherein AGO means hydrocarbon wherein ≥1.0 wt. %, e.g., 5.0 wt. %, such as 10.0 wt. % of the hydrocarbon's carbon atoms are included in an aromatic ring, based on the weight of the hydrocarbon).

The first mixture can comprise, e.g., upgraded natural gas (such as natural gas that has been sweetened and/or dehydrated). Besides methane, natural gas commonly includes other hydrocarbons (such as ethane and other alkanes), e.g., in amounts that can be less than, greater than, or substantially equal to the amount of methane in the natural gas on a weight basis.

Optionally, the first mixture further comprises diluent, e.g., ≥1.0 wt. % of diluent based on the weight of the first mixture. Suitable diluents (which can be a diluent mixture) include one or more of hydrogen sulfide, nitrogen ($N_2$), hydrogen sulfide, $C_{4+}$ mercaptans, amines, mixtures of amines, non-hydrocarbon non-volatiles (whether combustible or not) including refractory inorganics, such as refractory oxygenates, inert gas (including inert gas mixtures), etc. In an embodiment, the first mixture comprises ≤10.0 wt. % diluent based on the weight of the first mixture.

The first mixture can comprise, e.g., a total amount of non-combustible non-volatiles (e.g., ash; ASTM D-189), from all sources, that is ≤2.0 parts per million weight (ppmw) based on the weight of the first mixture, e.g., ≤1.0 ppmw. Optionally, the first mixture comprises a total amount of combustible non-volatiles (e.g., tar, asphaltenes, ASTM D-6560) in the first mixture, from all sources, ≤5 wt. % based on the weight of the hydrocarbon in the first mixture, e.g., ≤1.0 wt. %, such as ≤100.0 ppmw or ≤10.0 ppmw, provided the presence of the combustible non-volatiles does not result in ≥2.0 ppmw (e.g., ≥1.0 ppmw) based on the weight of the second mixture.

Optionally, at least 15.0 wt. % of the molecular hydrogen in the first mixture (based on the total weight of molecular hydrogen in the first mixture) is molecular hydrogen derived from the second mixture or one or more products thereof. In another embodiment, the first mixture comprises ≥50.0 ppm sulfur based on the weight of the first mixture.

In an embodiment, the first mixture has the following composition (a) the first mixture comprises (i) ≥10.0 wt. % of hydrocarbon, e.g., ≥25.0 wt. % hydrocarbon; (ii) ≥1.0 wt. % molecular hydrogen, e.g., ≥15.0 wt. % molecular hydrogen; and ≥1.0 wt. % oxygenate, e.g., ≥5.0 wt. % oxygenate, the weight percents being based on the weight of the first mixture. Optionally, the first mixture's hydrocarbon comprises (i) ≥25.0 wt. % methane (e.g., obtained from natural gas), e.g., ≥50.0 wt. % methane, such as ≥90.0 wt. % methane and/or (ii) ≥25.0 wt. % AGO, e.g., ≥50.0 wt. % AGO, such as ≥90.0 wt. % AGO; the weight percents being based on the weight of the first mixture's hydrocarbon. One feature of the invention is that a natural gas containing a significant amount of $CO_2$, e.g., ≥20.0 mole % $CO_2$ per mole of the natural gas, can be converted into technologically important products, such as terephthalic acid and polymer.

It has been observed that including ≥1.0 wt. % of oxygenate, e.g., water, in the first mixture and pyrolysing the first mixture under the specified conditions increases the second mixture's acetylene:ethylene molar ratio. This is generally desirable because the cyclooctatetraene is produced from the acetylene. For example, when the first mixture's hydrocarbon comprises ≥10.0 wt. % alkane (including isoalkane) having from 2 to 10 carbon atoms, the weight percent being based on the weight of the first mixture's hydrocarbon, it can be desirable for the first mixture to further comprise ≥1.0 wt. % oxygenate, based on the weight of the first mixture. Optionally, the oxygenate comprises ≥90.0 wt. % water, at least a portion of the water being obtained from the product. Alternatively, the oxygenate is derived from at least a second source material, e.g., one comprising one or more of oxygen ($O_2$), carbon monoxide, carbon dioxide, acid (e.g., organic acids such as hydrocarbon containing a carboxyl functionality), carbonyls, carbonates, carbamates, carbohydrates, non-volatile oxygenates, etc.

When the first mixture's oxygenate comprises ≥90.0 wt. % carbon monoxide based on the weight of the first mixture's oxygenate, the first mixture (i) has a ratio of oxygen atoms to carbon atoms ("O:C") ≥0.1, e.g., in the range of 0.1 to 2.0, such as in the range of 0.1 to 0.5, and (ii) comprises 10.0 wt. % to 95.0 wt. % hydrocarbon, e.g., 15.0 wt. % to 85.0 wt. %; 5.0 wt. % to 60.0 wt. % oxygenate, e.g., 10.0 wt. % to 60.0 wt. %; and 0.0 wt. % to 30.0 wt. % molecular hydrogen, e.g., 5.0 wt. % to 25.0 wt. %, the weight percents being based on the weight of the first mixture. The O:C atomic ratio is defined as the ratio of oxygen atoms (as the total number of oxygen atoms in the first mixture) to carbon atoms (as all carbon atoms in the first mixture that are not bound to oxygen atoms, e.g., as can be determined by Nuclear Magnetic Resonance Spectroscopy). For example, the denominator of this ratio can be equal to the number of carbon atoms bound to the first mixture's hydrocarbon. When an oxygenate other than carbon monoxide is utilized, the amount of oxygenate (as defined by the O:C ratio) is equal to (a) the amount of oxygenate that would have been used if the oxygenate were carbon monoxide divided by (b) the Effectiveness Factor corresponding to the oxygenate that is actually used. For example, the first mixture O:C ratio is set equal to (a) divided by (b), where (a) is the O:C ratio that would have been used if the oxygenate were carbon monoxide and (b) is the Effectiveness Factor corresponding to the oxygenate that is actually used. The Effectiveness Factor can be readily determined by one skilled in the art of pyrolysis as the fraction of the first mixture oxygenate oxygen atoms that emerge from pyrolysis as carbon monoxide molecules in the second mixture. The Effectiveness Factors for selected oxygenates is set out in the following table, those Effectiveness Factors being based on exposing a feed comprising methane, molecular hydrogen, and oxygenate, e.g., the first mixture, under a wide range of conditions effective to result in a 50 to 70% conversion of the methane, including peak pyrolysis temperatures ranging from 1400° C. to 1800° C., pressures from 1.3 to 2.0 bar (absolute), and residence times from about 1 to 50 millisecond. It has been found that the Effectiveness Factor, except for that of molecular oxygen, is approximately constant over this broad range, as long as conditions are effective to result in about 50 to 70% hydrocarbon conversion. While not wishing to be bound by any theory or model, it is believed that the variation observed in the Effectiveness Factor of molecular oxygen as a function of pyrolysis conditions results at least in part from the reaction of the molecular oxygen with the first mixture's hydrocarbon, which leads to changes in pyrolysis heat balance. When the oxygenate is a mixture of two or more oxygenates, the mixture's Effectiveness Factor is approximately equal to the linear combination of the individual oxygenate's Effectiveness Factors. For example, when the oxygenate is a mixture of X mole % of carbon monoxide, Y mole % of water, and Z mole % of carbon dioxide, the mixture's Effectiveness Factor=X·1.0+Y·0.05+Z·0.45. In an embodiment, the Effectiveness Factor is ≥0.10, e.g., ≥0.2, such as ≥0.4. In an embodiment, the oxygenate is one or more of water, molecular oxygen, carbon dioxide, or carbon monoxide. In an embodiment, the oxygenate is one or more of (i) a lower-cost oxygenate, such as air or water, or (ii) oxygenate such as carbon dioxide, that is naturally present in the hydrocarbon source material.

TABLE

| Oxygenate | Effectiveness Factor |
| --- | --- |
| Carbon Monoxide | 1.0 |
| Water | 0.05 |
| Molecular Oxygen ($O_2$) | 0.15 |
| Carbon Dioxide | 0.45 |
| Methanol | 0.95 |
| Ethanol | 0.65 |

The amount of oxygenate in the first mixture can be selected based on the amount of acetylene in the second mixture that will be utilized to produce the desired cyclooctatetraene to use in stage 216. Optionally, the amount of oxygenate in the second mixture is selected to be within approximately +/−25.0% (weight basis), e.g., +/−10.0%, of the amount of oxygenate needed to maximize the second mixture's acetylene:ethylene molar ratio, such as within +/−25.0% (weight basis) of the amount needed to convert ≥10.0 wt. % of the first mixture's hydrocarbon to acetylene based on the weight of the first mixture, such as 15.0 wt. %, or 20.0 wt. %.

A suitable process for deriving the second mixture from the first mixture will now be described in more detail. In this embodiment, the second mixture is derived from the first mixture by exposing the first mixture to pyrolysis conditions in a regenerative, reverse-flow pyrolysis reactor. The invention is not limited to this embodiment, and this description should not be construed as foreclosing other embodiments for deriving the second mixture, such as those utilizing other pyrolysis or partial oxidation reactors.

Regenerative, Reverse-flow Thermal Pyrolysis System

Figure 3:
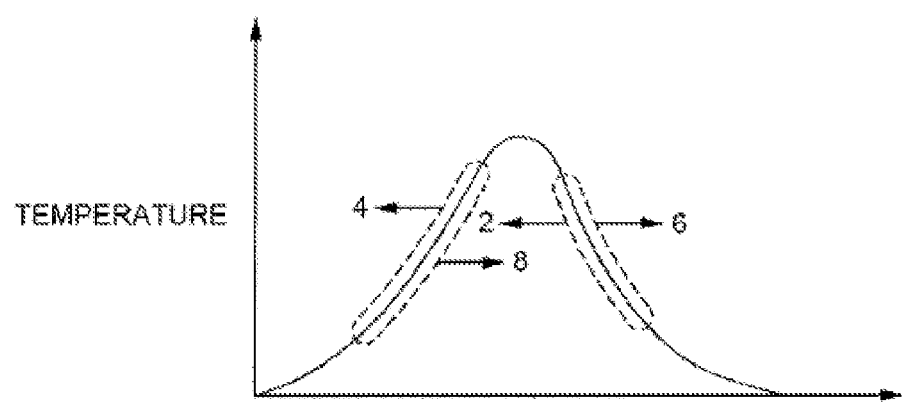
FIG. 3 schematically illustrates selected thermal properties of a regenerative, reverse-flow reactor.
Figure 3:
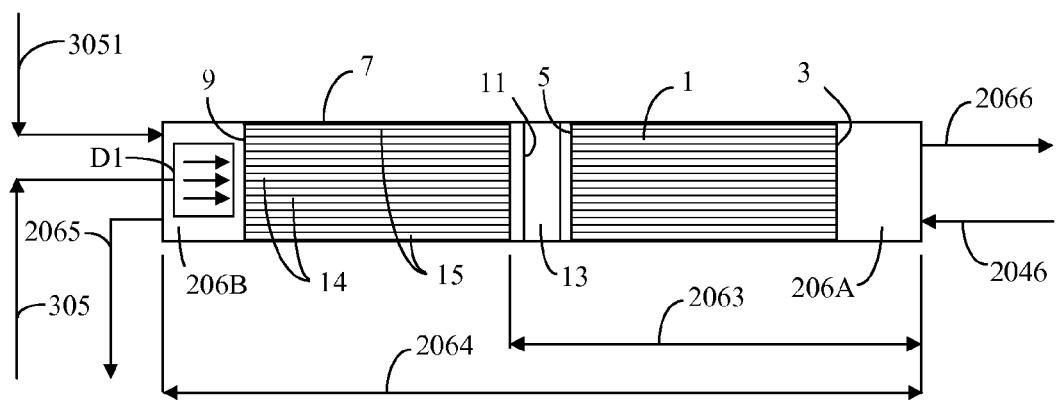

In certain embodiments, the second mixture is derived from the first mixture in a reverse-flow, regenerative bed reactor system. Such reactor systems can be used for operating (e.g., continuously or semi-continuously) a two-step asymmetric cycle reaction, e.g., a cycle comprising an oxidation (regeneration) step and a pyrolysis (reforming) step. Suitable reactor systems include those described in U.S. Patent Application Publication No. 2007/0191664; U.S. Pat. Nos. 7,491,250 and 7,943,808; U.S. Patent Application Ser. No. 61/349,464; and U.S. Patent Application Publication Nos. 2007/0144940 and 2008/0142409, all of which are incorporated by reference herein in their entirety. An example of a representative reverse-flow, regenerative bed reactor system is depicted in FIG. 3. The reactor comprises three zones, a first ("recuperator") zone 7, a mixing-distributing zone 13, and a second ("reaction") zone 1. Zones 1 and 7 each comprise at least one regenerative bed, where the term "regenerative bed" means a reactor bed comprising material that is effective in storing and transferring heat. In an embodiment, the regenerative beds comprise bedding or packing material, such as glass or ceramic beads (e.g., spheres), metal beads (e.g., spheres), ceramic (including, e.g., alumina, silica, yttria, zirconia, etc., and mixtures thereof) or metal honeycomb materials, ceramic tubes, extruded monoliths, catalysts, etc. The first and second reactor beds can be of the same shape and size, but this is not required. Zone 13 generally comprises at least one mixer-distributor for combining fuel and oxidant during regeneration of the regenerative, reverse-flow reactor system.

In an embodiment, at least one of the first or second reactor beds comprise a honeycomb monolith. Although honeycombs can have a circular cross-section, this is not required, and the term is not limited to any particular monolithic structure, shape, or topology. In embodiments where a honeycomb monolith is used, the honeycomb monolith is believed to enable low pressure loss transference while providing contact time and heat transfer.

The reactor system is heated for the pyrolysis step, with at least a portion of the heat utilized by the endothermic pyrolysis step being provided by the oxidation step. The heating can occur in exothermic reaction region 2063, which can be located, e.g., between a first point proximate to the downstream end 11 of first reactor 7 and a second point proximate to the downstream end 3 of second reactor 1; "downstream" in this case being with respect to the average flow of fuel and oxidant.

A first reactant, comprising, e.g., fuel, and a second reactant, comprising, e.g., an oxidant, such as air, are generally conducted to a location proximate to mixing zone 13. The first and second reactants are distributed and mixed as they traverse zone 13, and the combined reactants together with any oxidation products are then conducted away from zone 13 via passages in second reactor 1.

The oxidation step results in a high temperature zone in the reactor system's temperature profile, at least a portion of the high temperature zone being located in region 2063. The temperature profile is illustrated schematically as a Gaussian-like shape in FIG. 3.

The oxidation step thus includes the following features: (i) heating of zone 13 and the second reactor 1 by transferring at least a portion of the heat of combustion to the reactor system downstream of the end 11 of the first reactor 7 and (ii) by transferring at least a portion of the sensible heat recovered by the first and second reactants in an upstream region of the first reactor (upstream with respect to the flow of the first and second reactants) toward one or more of the downstream region of the first reactor, region 13, or the second reactor in order to thermally regenerate the reactor system. Accordingly, at least a segment of each of the right-hand and left-hand edges of the temperature profile translate downstream from their starting locations at the beginning of the oxidation step, as shown in FIG. 3 by arrows 6 and 8. After the reactor system is heated, the flow-direction of gases traversing the reactor system is reversed for the pyrolysis step. The oxidation step and pyrolysis step will now be described in more detail.

The Pyrolysis Step

At the start of the pyrolysis step, reaction zone 1 is at an elevated temperature, and the recuperator zone 7 is at a lower temperature than the reaction zone 1. The first mixture (the reactant feed, e.g., a pyrolysis feed) is introduced via a conduit 2046, into a first end 3 of the reaction zone 1.

In the embodiment of FIG. 3, the pyrolysis region 2064 can be located, e.g., between a first point proximate to the upstream end 3 of the second reactor 1 and a second point proximate to the downstream end 9 of first reactor 7, "upstream" and "downstream" being with respect to the average flow of the first mixture. It should be appreciated that the invention can be practiced without precisely defining (a) the boundaries of regions 2063 and 2064. Although region 2063 (the exothermic reaction region) is at least partially coextensive with pyrolysis region 2064, the upstream end of region 2063 ("upstream" with respect to the average flow of the fourth mixture) is generally proximate to the location where sufficient fuel and oxidant combine to produce an exothermic reaction. The downstream (with respect to the average flow of the first mixture) end of region 2063 is generally proximate to the downstream end of second reactor 1 as shown in FIG. 3, though this is not required, and in at least one embodiment the downstream end of region 2063 is located further downstream, e.g., in conduit 2066. In at least one of the embodiments represented by FIG. 3, the upstream end of pyrolysis region 2064 is proximate to the upstream end 3 of the second reactor 1. The downstream end of pyrolysis region 2064 can be, e.g., proximate to the downstream end 9 of the first reactor 7. Optionally, a major amount (e.g., ≥50%) of the heat abstracted from the reactor system during the pyrolysis occurs in the portion of region 2064 that is coextensive with region 2063.

The pyrolysis can be conducted, e.g., under high-severity pyrolysis conditions. The term "high-severity" with respect to the pyrolysis of a feed comprising hydrocarbon, e.g., the first mixture, means pyrolysis operating conditions resulting in the conversion to acetylene of ≥10.0 wt. % of the feed's hydrocarbon based on the total weight of hydrocarbon in the feed. The pyrolysis can be conducted under thermal pyrolysis conditions, e.g., high-severity thermal pyrolysis conditions.

In an embodiment, the first mixture is conducted to the pyrolysis stage 206 wherein it is exposed to a temperature≥$1.20\times10^{3}$° C. under thermal pyrolysis conditions, e.g., high-severity, thermal pyrolysis conditions, to convert at least a portion of the first mixture to the second mixture. At these conditions, ≥50.0 mole %, e.g., ≥60.0 mole %, such as ≥70.0 mole % of the first mixture's hydrocarbon is converted by the pyrolysis, per mole of the first mixture's hydrocarbon. At least a portion of the second mixture, e.g., a vapor-phase portion which comprises acetylene, ethylene, molecular hydrogen, and saturated hydrocarbon, is conducted away from the reactor system, e.g., to separation stage 208. A portion of the second mixture, e.g., a non-volatile portion (such as coke and/or soot) can remain in the stage 206, e.g., as a deposit.

In an embodiment, the pyrolysis is conducted under high-severity thermal pyrolysis conditions, e.g., by exposing the first mixture to a temperature in the range of about $1.40\times10^{3}$° C. to about $2.30\times10^{3}$° C., e.g., in the range of about $1.45\times10^{3}$° C. to about $1.80\times10^{3}$° C. at a residence time≤about 0.3 seconds, e.g., ≤0.05 seconds. Optionally, the residence time is ≤0.05 seconds, such as ≤0.02 seconds. Optionally, ≥25.0 wt. % (such as of the ≥50.0 wt. % or ≥75.0 wt. %) of the first mixture achieves a peak pyrolysis gas temperature≥$1.40\times10^{3}$° C., e.g., in the range of about $1.50\times10^{3}$° C. to about $1.675\times10^{3}$° C., based on the weight of the first mixture.

In an embodiment, the pyrolysis is conducted for a time duration ($t_1$) sufficient for exposing ≥50.0 wt. %, e.g., ≥75.0 wt. %, such as ≥90.0 wt. % of the first mixture (based on the weight of the first mixture) to pyrolysis conditions for a residence time≤about 0.3 seconds, e.g., ≤0.05 seconds. In an embodiment, $t_1$ is ≤10.0 seconds, e.g., ≤5.0 seconds, such as ≤1.0 seconds. Optionally, $t_1$ is in the range of $1.0\times10^{-3}$ seconds to 10.0 seconds.

In an embodiment, the pyrolysis step includes one or more of the following conditions: the first mixture achieves a peak pyrolysis gas temperature≥$1.40\times10^{3}$° C., e.g., in the range of $1.45\times10^{3}$° C. to $2.20\times10^{3}$° C., such as, $1.50\times10^{3}$° C. to $1.90\times10^{3}$° C., or $1.60\times10^{3}$° C. to $1.70\times10^{3}$° C.; a total pressure≥1.0 bar (absolute), e.g., in the range of 1.0 bar to about 15 bar, such as in the range of 2.0 bar to 10.0 bar; a residence time (during high severity conditions)≤0.1 seconds, e.g., ≤$5.0\times10^{-2}$ seconds, such as ≤$5.0\times10^{-3}$ seconds and/or a $t_1$ in the range of $1.0\times10^{-3}$ seconds to 10.0 seconds.

Continuing with reference to FIG. 3, the first mixture abstracts heat from the reactor system, resulting in the derivation of the second mixture from the first by pyrolysis. As this step proceeds, a shift in the temperature profile occurs, e.g., a shift in at least a segment of the right-hand edge of the temperature profile (the segment being schematically encompassed by a dashed boundary for the purpose of illustration), the direction of the shift being indicated by arrow 2. The amount of this shift can be influenced by, e.g., the heat transfer properties of the reactor system. At least a portion of the second mixture, e.g., the portion in the vapor phase, is conducted from the downstream end 5 of the second reactor 1 to the upstream end 11 of the first reactor 7, and is conducted away from the first reactor via conduit 2065 proximate to the downstream end 9, as shown. At the start of pyrolysis, the first reactor 7 has a temperature less than that of the second reactor 1. As the second mixture traverses the first reactor 7, the second mixture is quenched (e.g., cooled) to a temperature approaching that of the downstream end 9 of the first reactor. As the second mixture is quenched in the first reactor 7, at least a segment of the left-hand edge of the temperature profile moves toward the downstream end 9 of the first reactor 7 as indicated by arrow 4, the segment being schematically encompassed by a dashed boundary for the purpose of illustration. In at least one of the embodiments represented by FIG. 3, the upstream end of pyrolysis region 2064 is proximate to the upstream end 3 of the second reactor 1. The downstream end of pyrolysis region 2064 is proximate to the downstream end 9 of the first reactor 7. Since the quenching heats the first reactor 7, the oxidation step optionally includes cooling the first reactor, e.g., to shift at least a segment of the left-hand edge of the temperature profile away from end 9 of the first reactor 7, as illustrated schematically by arrow 8 in FIG. 3.

The second mixture produced by pyrolysing the specified first mixture under the specified pyrolysis conditions will now be described in more detail.

The Second Mixture

When the specified first mixture is pyrolysed under the specified pyrolysis conditions, the second mixture comprises molecular hydrogen and ≥1.0 wt. % of acetylene based on the weight of the second mixture. Optionally, the second mixture has one or more of the following additional properties: an acetylene:ethylene molar ratio≥0.5, such as in the range of about 0.5 to about 20.0, e.g., about 1.20 to about 10.0, or about 2.0 to about 10.0; a molecular hydrogen:acetylene molar ratio≥0.1, or ≥0.75, or ≥3.0, e.g., in the range of 3.0 to 20.0; a water content≤50.0 wt. % based on the weight of the second mixture, e.g., 25.0 wt. %, such as ≤10.0 wt. %; or a carbon dioxide:$C_2$ unsaturates molar ratio≤1.0, e.g., ≤0.30. Optionally, the second mixture comprises ≥1.0 wt. %, methane e.g., 2.0 wt. % to 50.0 wt. %; ≥1.0 wt. % carbon monoxide, e.g., 2.0 wt. % to 50.0 wt. %, such as 5.0 wt. % to 35.0 wt. %; ≥1.0 wt. % molecular hydrogen, e.g., 2.0 wt. % to 50.0 wt. %; ≥2.0 wt. % acetylene, e.g., 2.0 wt. % to 40.0 wt. %; ≥1.0 wt. % ethylene, e.g., 2.0 wt. % to 70.0 wt. %, such as 2.0 wt. % to 20.0 wt. %; and ≥1.0 wt. % $C_{3+}$, e.g., 2.0 wt. % to 50.0 wt. %, the weight percents being based on the weight of the second mixture. Optionally, the mole percents of molecular hydrogen and acetylene in the second mixture are in the following ranges: molecular hydrogen in the range of from about 1.0 mole % to 98.0 mole %, e.g., about 2.0 mole % to about 95.0 mole %, such as about 10.0 mole % to 80.0 mole %; and acetylene in the range of from about 0.1 mole % to 35.0 mole %, such as from about 1.0 mole % to 35.0 mole %, the mole percents being based on the number of moles of molecular hydrogen and acetylene per mole of the second mixture.

Optionally, the first mixture comprises ≥1.0 wt. % oxygenate based on the weight of the first mixture, e.g., ≥2.0 wt. %, such as ≥5.0 wt. %, and the second mixture has an acetylene:ethylene molar ratio≥2.0, e.g., ≥4.0 such as ≥6.0.

In certain embodiments, at least a portion of the second mixture's non-volatiles remain in stage 206, e.g., as coke or soot. At least a portion of the second mixture, e.g., a portion that is in the vapor phase at the downstream end of stage 206, is conducted to stage 208 as shown in FIGS. 1 and 2.

Producing the second mixture from the first mixture by pyrolysis is an endothermic reaction, which withdraws heat from the pyrolysis reactor system. When the reactor system is cycled continuously or semi-continuously, at least a portion of the heat utilized by the pyrolysis steps is replaced by heat produced during the intervening oxidation steps, with one cycle of the reactor system comprising an oxidation step and a pyrolysis step. The oxidation (regeneration) step will now be described in more detail with reference to FIGS. 2, 3, and 4.

The Oxidation Step

Regeneration entails transferring heat from (i) the mixing-distributing zone 13 and optionally (ii) from recuperator zone 7 to the reaction zone 1, to thermally regenerate the reactor system for a pyrolysis step. A fourth mixture, (the regeneration gas, e.g., the combustion gas) is produced proximate to zone 13 by mixing and distributing the first and second reactants, e.g., fuel and oxidant. The first reactant (comprising fuel) is conducted to recuperator zone 7 via conduit 305. The second reactant (comprising oxidant) is conducted to recuperator zone 7 via conduit 3051. Optionally, first distribution means (D1) can be utilized for conducting the first reactant into fuel passages 14 and/or second distributor means (e.g., plenum 206B) can be utilized for conducting the second reactant into oxidant passages 15, the fuel passages and oxidant passages being located within recuperator zone 7. Since the fuel and oxidant passages are substantially independent flow paths (e.g., there is little or no fluid communication one with the other) mixing of the first and second reactants generally does not occur until zone 13, where the first and second reactants combine to produce the fourth mixture. A fifth mixture, derived from at least in part from the oxidation of at least a portion of the fourth mixture's fuel component, is conducted away from the reactor system via plenum 206A and conduit 2066.

The first and second reactants exit recuperator zone 7, and combine in zone 13 to produce the fourth mixture. By keeping these reactants substantially separated upstream of zone 13, upstream with respect to the average flow of the first and second reactants, the heat (i) conveyed from the recuperator zone toward the regenerator zone and (ii) released during the exothermic reaction is directed towards regions of the reactor system that are beneficial for the pyrolysis. The term "substantially separated" means that ≤50.0 wt. %, e.g., ≤25.0 wt. %, of the first reactant's fuel component is consumed by reaction with the second reactant's oxidant component upstream of zone 13, based on the weight of the first reactant's fuel component conveyed to distributor (D1). In this manner, the majority of the heat released from the reaction of the fourth mixture's fuel and oxidant components will not take place until the gases have exited from the recuperator zone 7 into mixing-distributing zone 13. Optionally, passages 14 and 15 of recuperator zone 7 are oriented substantially parallel to the direction of the average flow of fuel and oxidant. Such passages are provided, for example, by regenerative beds comprised of extruded honeycomb monoliths, packing, stacked layers of corrugated materials, etc. When the recuperator zone 7 includes a packed bed or foam monolith materials (not shown), these bed materials should be configured to keep the first and second reactants substantially separated. Radial dispersion and the amount of first-reactant-second reactant mixing can be measured and/or calculated as described in U.S. Pat. No. 7,815,873.

Figure 4:
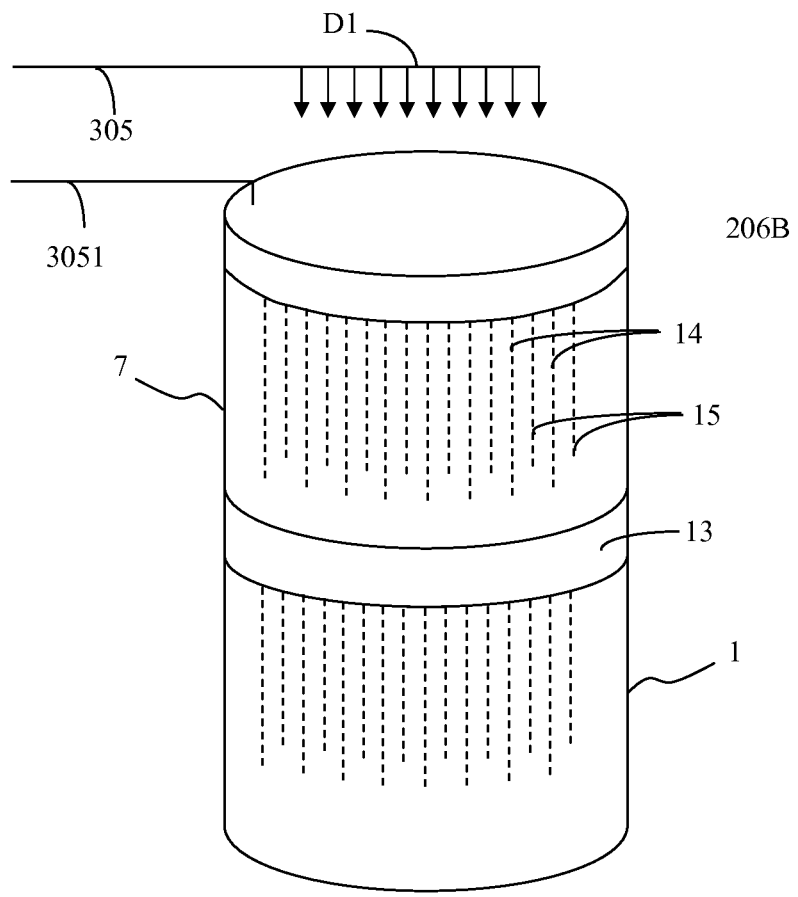
FIG. 4 schematically illustrates a sparger suitable for use with a reverse-flow pyrolysis reactor.
Figure 4A:
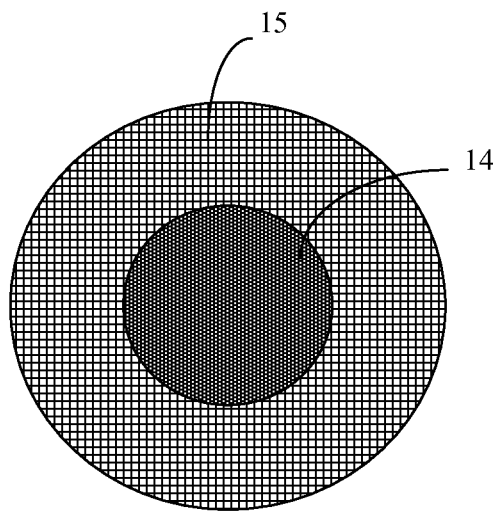
FIG. 4A schematically shows an end-view of such a reactor.

FIGS. 3 and 4 schematically show a flow distributor D1 for directing fuel into passages 14 which have a plurality of apertures (shown as small arrows in FIGS. 3 and 4) aligned with passages 14. Plenum 206B provides for the flow of oxidant into passages 15. The apertures of D1 can be aligned with, but are not sealed to, the openings of channel 15. By not "sealing" D1's apertures to passages 14, passages 14 and 15 may be utilized during the reverse flow or reaction cycle, increasing the overall efficiency of the system. This "open" distributor (D1) can also be utilized in embodiment comprising multiple pyrolysis reactor systems, e.g., those where the reactor/recuperator beds move (e.g., rotate) in and out of a gas stream. FIG. 4A schematically shows an end view of reactor 7, with the shaded regions representing the approximate locations of distributor D1 (utilized to direct fuel into passages 14). The unshaded region corresponds to the approximate locations of passages 15, which are utilized during the oxidation step for conveying oxidant from conduit 3051 to region 13.

During the oxidation step, fuel and oxidant transit the recuperator zone 7, abstracting at least a portion of the heat, stored in the recuperator zone from previous pyrolysis steps. The heated reactants (fuel and oxidant) are then introduced into zone 13 as shown in FIGS. 3 and 4. Mixer-distributor means can be utilized in zone 13 to produce the fourth mixtures by combining the first and second reactants emerging from recuperator zone 7, and then distributes the fourth mixture, particularly the fourth mixture's fuel and oxidant components to achieve a more uniform oxidation over the reactor system's cross-section upstream of reaction zone 1. The fourth mixture's oxidant component reacts with (i) the fourth mixture's fuel component and (ii) combustible non-volatiles located in the reactor system to produce a fifth mixture, which can further comprise unreacted fourth mixture, if any.

The total duration of an oxidation step $t_2$ is generally greater than or equal to the time needed for the second reactor to abstract sufficient heat from the oxidation to accomplish the pyrolysis step. In other words, the oxidation step is conducted for a time duration greater than or equal to a time sufficient to displace the peak of the temperature profile toward the second reactor sufficient to heat the pyrolysis region 2064 for exposing the first mixture to a temperature $\geq 1.20 \times 10^{3}$° C. during the pyrolysis step. The value of $t_2$ depends on factors, such as the geometry of the reactors utilized in stage 206, the heat transfer characteristics of the reactors and the materials from which the reactors are made, and the amount of heat needed by the pyrolysis step. Optionally, the $t_2$ is in the range of $1.0 \times 1.10^{-3}$ seconds to 10.0 seconds. In an embodiment, $t_2$ is greater than or equal to the time needed to heat the pyrolysis region 2063 to a temperature sufficient for exposing $\geq 50.0$ wt. % of the first mixture, e.g., $\geq 75.0$ wt. %, such as $\geq 90.0$ wt. % to a temperature $\geq 1.20 \times 10^{3}$° C. during the pyrolysis step; the weight percents being based on the weight of the first mixture. In an embodiment, $t_2$ is $\leq 10.0$ seconds, e.g., $\leq 5.0$ seconds, such as $\leq 1.0$ seconds.

It is understood that flow control means (e.g., one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optional purge gas when used between one or more of the steps. Suitable spargers, distributors, etc., are disclosed in U.S. Pat. No. 7,815,873, which is incorporated by reference herein in its entirety. Although the invention is compatible with the use of conventional spargers, distributors, plenums, etc., in stage 206, the invention is not limited thereto. The fourth and fifth mixture will now be described in more detail.

The Fourth Mixture

The fourth mixture comprises first and second reactants. The first reactant can comprise, e.g., $\geq 10.0$ wt. % fuel based on the weight of the first reactant, such as $\geq 50.0$ wt. % fuel. The second reactant can comprise, e.g., $\geq 10.0$ wt. % oxidant based on the weight of the second reactant, such as $\geq 20.0$ wt. % oxidant. The first reactant can be derived from the same source materials utilized for deriving the first mixture. Optionally, the first reactant has substantially the same composition as the first mixture.

Referring again to FIG. 2, stage 302 can be utilized for adjusting the compositions of source materials 300 to produce the fuel and/or oxidant. Generally, separate fuel and oxidant conduits are utilized (not shown), and optionally, the fuel source material is upgraded in a stage (e.g., 302a, not shown) that is different from that used to upgrade the oxidant (302b, not shown). Conduits (represented by line 3021) can be utilized for adding to the fuel source materials one or more of diluent, carbon monoxide, molecular hydrogen, and/or light saturated hydrocarbon. Conduits (also represented by line 3021) can be utilized for adding additional or supplemental oxidant to the oxidant source materials. Undesired species, such as heteroatom species, can be conducted away from stage 302 by one or more conduits (not shown).

The fuel and oxidant can be the same as those disclosed in U.S. Pat. No. 7,943,808. Optionally, the fuel is derived from, comprises, consists essentially of, or consists of one or more of hydrogen, CO, methane, methane containing streams, such as coal bed methane, biogas, associated gas, natural gas, and mixtures or components thereof, etc. Exothermically reacting the first reactant's fuel component and the second reactant's oxidant component provides at least a portion of the heat utilized by the pyrolysis, e.g., $\geq 50\%$, such as $\geq 75\%$, or $\geq 95\%$ of the heat utilized by the pyrolysis. Additional heat, when needed, can be provided to the regenerative, reverse-flow pyrolysis reactor by, e.g., a burner or furnace, e.g., a furnace external to the reactor, but in thermal communication therewith. The first and second reactants mix within the regenerative, reverse-flow pyrolysis reactor to produce the fourth mixture, the fuel and oxidant then reacting, e.g., by an oxidation reaction, such as combustion, as the fourth mixture traverses at least a portion of the pyrolysis reactor. The first reactant comprises fuel, e.g., molecular hydrogen, synthesis gas (mixtures of CO and $H_2$), or hydrocarbon, such as $\geq 10.0$ wt. % hydrocarbon (including mixtures thereof), or $\geq 50.0$ wt. % hydrocarbon, or $\geq 90.0$ wt. % hydrocarbon based on the weight of the first reactant. The second reactant comprises oxidant, e.g., molecular oxygen.

The amount of oxidant in the second reactant and the relative amounts of first and second reactants utilized to produce the fourth mixture can be specified in terms of the amount of oxidant in the second reactant needed for oxidizing combustible non-volatiles in the reactor system ("X") and the amount needed for the substantially stoichiometric oxidation of the first reactant's fuel component ("Y"). In an embodiment, the total amount of oxidant in the fourth mixture is Z(X+Y), wherein Z is in the range of 0.8 to 10.0, e.g., in the range of 1.0 to 3.0, and the amounts X and Y are on a molar basis. When Z>1.0, the excess oxidant can be utilized, e.g., for moderating the reaction temperature during the oxidation step as disclosed in U.S. Pat. No. 7,943,808, and/or for conveying heat within the reactor system.

The fourth mixture is generally produced in the mixing-distribution zone, the mixing-distribution zone being located downstream of the first reactor's channels. Although the fourth mixture comprises the combination of first reactant and second reactants, the combined stream generally includes species resulting from the oxidation of combustible non-volatiles located in the first reactor's passages. Optionally, the combined stream further comprises species resulting from reaction of the first and second reactants in one or more of the first reactor's channels, or locations upstream thereof, as a result of comingling of the first and second reactants. Generally, the amount of comingling is small, as disclosed in U.S. Pat. No. 7,943,808. It can be beneficial for the amount of oxidant in the fourth mixture to exceed that needed to oxidize substantially all of the fourth mixture's fuel component, e.g., for (i) oxidizing combustible non-volatiles located in regions of the reactor system downstream of the first reactor's channels, (ii) moderating the temperature during the oxidation of the fourth mixture's fuel component, and/or (iii) transferring heat within regions of the reactor system downstream of the mixing-distribution zone. The desired amount of excess oxygen can be provided by increasing the relative amount of oxidant in the second reactant and/or by increasing the relative amount of second reactant in the fourth mixture.

Optionally, the fourth mixture further comprises diluent, e.g., ≥1.0 wt. % of diluent based on the weight of the fourth mixture. Suitable diluents (which can be a diluent mixture) include one or more of, e.g., oxygenate (water, carbon dioxide, etc.), non-combustible species, such as molecular nitrogen ($N_2$), and fuel impurities, such as hydrogen sulfide. In an embodiment, the fourth mixture comprises ≤96.0 wt. % diluent, e.g., in the range of 50.0 wt. % to 95.0 wt. % diluent, based on the weight of the fourth mixture. In an embodiment, diluent is provided to the fourth mixture as a component of the second reactant. For example, the second reactant can comprise 60.0 mole % to 95.0 mole % diluent and 5.0 mole % to 30.0 mole % oxidant per mole of the second reactant, such as when the second reactant is air. Optionally, the second reactant has a mass ratio of diluent to oxidant in the range of 0.5 to 20.0, e.g., in the range of 4.0 to 12.0. It can be beneficial for the second reactant (and fourth mixture) to further comprise diluent, e.g., for (i) moderating the temperature during the oxidation of the fourth mixture's fuel component and/or (ii) transferring heat within the reactor system.

In an embodiment, the first reactant comprises ≥90.0 wt. % molecular hydrogen based on the weight of the first reactant and the second reactant comprises ≥90.0 wt. % air based on the weight of the second reactant. When the second reactor comprises ≥90.0 wt. % air based on the weight of the second reactant, a fourth mixture produced from these can comprise, e.g., ≥1.0 wt. % molecular oxygen, e.g., in the range of 5.0 wt. % to 25.0 wt. %, such as 7.0 wt. % to 15.0 wt. %; ≥0.1 wt. % fuel, e.g., in the range of 0.2 wt. % to 5.0 wt. %, the weight percents being based on the weight of the fourth mixture, with the balance of the fourth mixture being molecular nitrogen diluent, e.g., ≥50.0 wt. % diluent, such as in the range of 60.0 wt. % to 94.50 wt. % diluent based on the weight of the fourth mixture.

In an embodiment, the mass flow rate of the fourth mixture during the oxidation step is ≥1.0 times the flow rate of the first mixture during the pyrolysis step, e.g., in the range of 1.0 to 6.0 times the flow rate of the first mixture during the pyrolysis step.

The Fifth Mixture

The fifth mixture comprises (i) products derived from the exothermic reaction of the fourth mixture's fuel and oxidant with each other and with the combustible non-volatiles within the reactor, optionally (ii) diluent, when diluent is present in the fourth mixture, and/or (iii) unreacted fuel and oxidant. When the exothermic reaction of the fuel and oxidant involves hydrocarbon combustion, or when a diluent is present in the fourth mixture (such as $N_2$ or $H_2S$), the fifth mixture can comprise carbon dioxide, and can further comprise sulfur oxides, nitrogen oxides, etc.

As shown in FIG. 2, the process can also include an upgrading stage 308 for upgrading the fifth mixture downstream of conduit 2066. One or more conduits 3081 can be utilized for conducting away combustion products and upgraded combustion products away from stage 308, e.g., one or more of non-oxidized hydrocarbon, oxygenate, or heteroatom species, such as $NO_x$, $SO_x$, $N_2$, sulfuric acid, etc.

Stages Downstream of the Pyrolysis Stage

As shown in FIG. 2, the second mixture or a vapor-phase component thereof is conducted away from stage 206 via conduit 2065 to stage 208, stage 208 being utilized at least for separating acetylene from the second mixture, e.g., by solvent extraction. In certain embodiments, the catalyst utilized in stage 212 is tolerant of molecules, such as ethylene, methane, ethane, oxygenate (water, carbon monoxide, etc.), mercaptan, etc., that may be present in the second mixture. In such embodiments, separation stage 208 is optional, with these molecules and unconverted acetylene being separated from the cyclooctatetraene downstream of stage 212, e.g., in stages 214 and/or 218. The following description concerns an embodiment utilizing separation stage 208 for separating acetylene from the vapor-phase portion of the second mixture.

Acetylene can be extracted from the vapor-phase portion of the second mixture in stage 208 using a polar fluid, the polar fluid being conducted to stage 208 via conduit 2086. At least a portion of the extract's acetylene is then removed from the polar fluid to produce the cyclooctatetraene in stage 212; optionally, at least a portion of the polar fluid is returned to line 2086 for re-use, as shown. The acetylene is conducted away from stage 208 via conduit 2087. The polar fluid can remove, e.g., ≥50.0 wt. %, e.g., ≥90.0 wt. %, such as ≥95.0 wt. % of the second mixture's acetylene, based on the weight of the second mixture's acetylene. The polar fluid can comprise, e.g., one or more of furfural, phenol, n-methyl-2-pyrrolidone, methanol, acetone, or tetrahydrofuran. Suitable polar fluids are disclosed in U.S. Pat. Nos. 3,093,697; 3,617,495; 4,274,841; and 7,045,670, which are incorporated by reference herein in their entirety. At least a portion of the raffinate is conducted away from stage 208 via conduit 2081.

Stage 208 can have, e.g., at least two broad functions. The first function is to remove poisons, impurities (e.g., hydrogen sulfide), or excess species (e.g., molecular hydrogen) that are not needed by downstream conversion, and the second function is to direct by splitting or separating the flows of downstream reactants (e.g., acetylene, molecular hydrogen, etc.) to designated conversion stages (e.g., 212). The functions may be effected in any order, and may be effected by single or multiple process steps. The first function may be applied even when no division of the downstream reactants is made and/or prior to or after the splitting and separating of downstream reactants. Heteroatom species and olefin (such as ethylene) can be conducted away from stage 208 via one or more conduits 2082.

Acetylene is conducted to stage 212 for conversion to a conversion product comprising aromatics, e.g., converting to cyclooctatetraene≥10.0 wt. % of the separated acetylene based on the weight of the separated acetylene, such as ≥25.0 wt. %, or ≥50.0 wt. %. Optional stage 214 can be utilized for removing and conducting away via conduit 2142 molecules, that are not needed in stages downstream of stage 212, e.g., unconverted feed molecules, such as acetylene, byproducts, such as molecular hydrogen, benzene, ethylene, ethane, and/or methane, etc.

Conventional methods can be utilized for converting at least a portion of the separated acetylene to cyclooctatetraene in stage 212, but the invention is not limited thereto. Suitable acetylene conversion methods are disclosed, e.g., in U.S. Pat. Nos. 2,903,491 and 2,951,881. These methods can involve diluting the acetylene with, e.g., inert gases or dissolved in solvents to keep it out of the decomposition regime, as disclosed in U.S. Pat. No. 2,912,472.

One acetylene conversion process includes catalytically converting ≥50.0 wt. % of the second mixture's acetylene in the presence of a catalytically effective amount of a first catalyst comprising nickel, e.g., ≥0.1 wt. % nickel based on the weight of the first catalyst. The first catalyst can comprise nickel acetylacetonate, for example. The catalytic conversion conditions can include a temperature in the range of 65° C. to 140° C. and a pressure≥1.0 bar (absolute), e.g., in the range of 1.0 bar (absolute) to 200 bar (absolute). Generally, the products of the acetylene conversion are components of a mixture (the third mixture). Besides cyclooctatetraene produced in the acetylene conversion, the third mixture can further comprise, e.g., benzene, unreacted acetylene, etc. For example, the cyclooctatetraene can constitute ≥10.0 wt. % of the third mixture, the third mixture (i) being derived from the conversion of the separated acetylene and (ii) further comprising unreacted separated acetylene.

In certain embodiments, the third mixture is conducted to optional separation stage 214, for separating from the third mixture≥90.0 wt. % of the third mixture's cyclooctatetraene based on the weight of the third mixture. The separated cyclooctatetraene can be conducted to stage 216 via one or more conduits 2141. Stage 216 is utilized for converting at least a portion of the separated cyclooctatetraene to a product comprising water and ≥10.0 wt. % phthalic acid, based on the weight of the product, such as 10.0 wt. % terephthalic acid. Conventional methods can be utilized for converting the cyclooctatetraene to phthalic acid and water, but the invention is not limited thereto. Suitable methods include those described in the G. L. Fray and R. G. Saxton reference, supra, and in "Oxidation of Cyclooctatetraene to the Tropylium Cation" Ganellin, C. R.; Pettit, R. *Journal of the American Chemical Society*, Vol. 79, Issue 7 (1957) pp. 1767-1768.

In certain embodiments, the cyclooctatetraene converting is catalytic conversion, utilizing a second catalyst, the second catalyst comprising chromium. For example, the catalyst can comprise ≥1.0 wt. % of chromium atoms that are bound to at least one oxygen atom, the weight percent being based on the weight of the catalyst, such as a catalyst comprising ≥1.0 wt. % chromic acid based on the weight of the catalyst. When a chromic acid catalyst is used, the conversion can be conducted under conditions including a temperature in the range of 0° C. to 150° C., a pressure in the range of 0.1 bar to 100 bar, and a space velocity in the range of 0.1 LHSV to 2000 LHSV.

One example of such a conversion process operates by oxidizing the cyclooctatetraene with acetic acid and/or hydrogen peroxide. When hydrogen peroxide is utilized, the molar ratio of hydrogen peroxide to cyclooctatetraene is optionally in the range of 0.5 to 5.0. Hydrogen peroxide reacts with the cyclooctatetraene to produce an oxidized $C_8$ molecule:

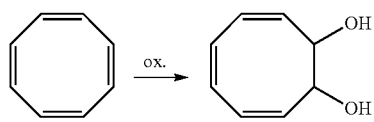 [SMILES: C1=C\C=C/C=C\C=C/1 ; OC1\C=C/C=C\C=C/C1O]

Hydrogen is available, e.g., from the chromic acid, to convert one OH group, yielding water and a $C_7$ aldehyde:

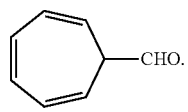

Hydrogen peroxide oxidizes the $C_7$ aldehyde to $C_7$ carbonyl and oxidize the opposite side of the $C_7$ to yield:

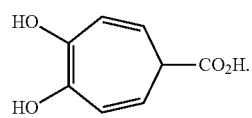

Hydrogen reacts with one of the opposite OH groups to produce water and

which can then be oxidized to terephthalic acid

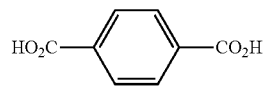

and/or hydrogen peroxide to produce the phthalic acid. Generally, ≥1.0 wt. % of the cyclooctatetraene in the feed to stage 216 is converted in stage 216 to phthalic acid, based on the total weight of cyclooctatetraene in the feed to stage 216. For example, ≥5.0 wt. % of the cyclooctatetraene conducted from stage 212 to stage 216 via conduits 2121 and 2141 can be converted to phthalic acid in stage 216, e.g., 5.0 wt. % to 10.0 wt. %.

At least a portion of the products of stage 216 and optionally any unconverted cyclooctatetraene are conducted away from state 216 via one or more conduits 2161, as shown in FIG. 2. Optional stage 218 can be utilized for separating at least a portion of the phthalic acid to produce a phthalic acid product comprising ≥50.0 wt. % terephthalic acid, e.g., ≥75.0 wt. %, such as ≥90.0 wt. % terephthalic acid, based on the weight of the phthalic acid product. The phthalic acid product can be conducted away from stage 218 via one or more conduits 2181, e.g., for storage and/or further processing to produce, e.g., polymer, such as synthetic fiber. Byproducts produced in state 216 (e.g., water) and any unreacted cyclooctatetraene can be conducted away from the process via one or more conduits 2182. If desired, other products of the pyrolysis of stage 206, e.g., ethylene, can be separated in stage 208, and conducted away via one or more conduits 2081. When it is deniable to produce additional polymer, optional stage 210 can be utilized for polymerizing at least a portion of the separated ethylene to produce polyethylene.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein, but rather that the claims be construed as encompassing all inventive features which reside herein, including all features which would be treated as equivalents thereof by those skilled in the art to which this disclosure pertains.

When numerical lower limits and numerical upper limits are listed herein, ranges from any lower limit to any upper limit are contemplated. Each of the following terms written in singular grammatical form: "a," "an," and "the," as used herein, may also refer to, and encompass, a plurality of the stated entity or object, unless otherwise specifically defined or stated herein, or, unless the context clearly dictates otherwise.

Each of the following terms: "includes", "including", "has", "having", "comprises", and "comprising", and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein. Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

The invention claimed is:

1. A hydrocarbon conversion process, comprising:
   (a) providing a first mixture comprising ≥1.0 wt. % hydrocarbon and ≥1.0 wt. % oxygenate, the weight percents being based on the weight of the first mixture, wherein the oxygenate comprises water obtained from step (d);
   (b) exposing the first mixture to a temperature ≥700° C. under pyrolysis conditions to produce a second mixture, wherein (i) the second mixture comprises ≥1.0 wt. % acetylene based on the weight of the second mixture and (ii) ≥95.0 wt. % of the second mixture's acetylene, based on the weight of the second mixture's acetylene, is produced by conversion of at least a portion of the first mixture's hydrocarbon;
   (c) converting ≥10.0 wt. % of the second mixture's acetylene to cyclooctatetraene, based on the weight of the second mixture's acetylene, in the presence of a catalyst comprising nickel in order to produce a third mixture, the third mixture comprising at least a portion of the cyclooctatetraene produced by the acetylene conversion; and
   (d) converting ≥5.0 wt. % of the third mixture's cyclooctatetraene to water and phthalic acids, based on the weight of the third mixture's cyclooctatetraene.

2. The process of claim 1, wherein the pyrolysis conditions include thermal pyrolysis conditions.

3. The process of claim 1, wherein the pyrolysis conditions include high-severity pyrolysis conditions.

4. The process of claim 1, wherein the first mixture's hydrocarbon comprises ≥95.0 wt. % methane, based on the weight of the first mixture's hydrocarbon, and wherein the pyrolysis conditions include conversion of 50.0 wt. % to 70.0 wt. % of the first mixture's methane, a peak pyrolysis temperature ranging from 1400° C. to 1800° C., a pressure in the range of from 1.3 bar (absolute) to 2.0 bar (absolute), and a first mixture residence time in the range of from about 1.0 milliseconds to 50.0 milliseconds.

5. The process of claim 1, wherein the second mixture has an acetylene:ethylene molar ratio in the range of 2.0 to 10.0 and a molecular hydrogen:acetylene molar in the range of 3.0 to 20.0.

6. The process of claim 1, wherein the second mixture comprises 2.0 wt. % to 50.0 wt. % methane; 2.0 wt. % to 50.0 wt. % molecular hydrogen; 2.0 wt. % to 40.0 wt. % acetylene; 2.0 wt. % to 20.0 wt. % acetylene; and ≥1.0 wt. % $C_{3+}$, the weight percents being based on the weight of the second mixture.

7. The process of claim 5, further comprising separating from the second mixture (i) ≥50.0 wt. % of the second mixture's molecular hydrogen, (ii) ≥90.0 wt. % of any oxygen-containing molecules contained in the second mixture, and (iii) ≥90.0 wt. % of the second mixture's $C_{3+}$, the weight percents being based on the weight of the second mixture; the separating being conducted before the converting of step (c).

8. The process of claim 5, further comprising separating from the second mixture (i) ≥50.0 wt. % of the second mixture's molecular hydrogen, (ii) ≥90.0 wt. % of any oxygen-containing molecules contained in the second mixture, and (iii) ≥90.0 wt. % of the second mixture's $C_{3+}$, the weight percents being based on the weight of the second mixture; the separating being conducted during and/or after the converting of step (c).

9. The process of claim 1, wherein (i) during step (c) ≥50.0 wt. % of the second mixture's acetylene is catalytically converted to the cyclooctatetraene, and (ii) the first catalyst of step (c) comprises ≥0.1 wt. % nickel based on the weight of the first catalyst.

10. The process of claim 9, wherein the first catalyst comprises nickel acetylacetonate.

11. The process of claim 10, wherein the catalytic conversion conditions of step (c) include a temperature in the range of 65° C. to 140° C. and a pressure in the range of 1.0 bar (absolute) to 200 bar (absolute).

12. The process of claim 9, wherein the cyclooctatetraene constitutes ≥10.0 wt. % of a third mixture, the third mixture (i) being derived from the conversion of step (c) and (ii) further comprising unreacted acetylene.

13. The process of claim 12, further comprising separating from the third mixture ≥90.0 wt. % of the third mixture's cyclooctatetraene based on the weight of the third mixture.

14. The process of claim 1, wherein the converting of step (d) includes catalytic conversion, the catalyst comprising ≥1.0 wt. % of chromium atoms that are bound to at least one oxygen atom based on the weight of the catalyst.

15. The process of claim 1, wherein the converting of step (d) includes catalytic conversion, the catalyst comprising ≥1.0 wt. % chromic acid based on the weight of the catalyst.

16. The process of claim 1, wherein the converting of step (d) includes a temperature in the range of 0° C. to 150° C., a pressure in the range of 0.1 bar to 100 bar, and a space velocity in the range of 0.1 LHSV to 2000 LHSV.

17. The process of claim 1, wherein the conversion of step (d) includes oxidizing at least a portion of the cyclooctatetraene utilizing acid and/or hydrogen peroxide to produce the phthalic acid.

18. The process of claim 17, wherein the oxidant is acetic acid and/or hydrogen peroxide.

19. The process of claim 18, wherein the oxidant is hydrogen peroxide, and the molar ratio of hydrogen peroxide to cyclooctatetraene in step (d) is in the range of 0.5 to 5.0.

20. The process of claim 1, wherein the pyrolysis is conducted in a first region, and further comprising:
  (e) providing a fourth mixture, and at least partially oxidizing the fourth mixture in a second region to produce a fifth mixture, the first and second regions being at least partially coextensive;
  wherein:
    (i) the fourth mixture comprises fuel and oxidant;
    (ii) the fifth mixture comprises water; and
    (iii) the exposing of the first mixture and the oxidizing of the fourth mixture occur at substantially different times.

21. The process of claim 20, further comprising repeating steps (a)-(e) in sequence, wherein (i) at least a portion of the fifth mixture is conducted away from the second region before step (a) and (ii) the exposure temperature in the first region results at least in part from the heat generated during the oxidizing of the fourth mixture in the second region.

* * * * *